US 6,517,845 B1

(12) United States Patent
Lee et al.

(10) Patent No.: US 6,517,845 B1
(45) Date of Patent: Feb. 11, 2003

(54) MYCOBACTERIUM TUBERCULOSIS SUPEROXIDE DISMUTASE

(75) Inventors: Fang-Jen S. Lee, Taipei (TW); Chung-Hsiun H. Wu, Taipei (TW)

(73) Assignee: Yung Shin Pharmaceutical Ind. Co., Ltd., Taipei (TW)

( * ) Notice: Subject to any disclaimer, the term of this patent is extended or adjusted under 35 U.S.C. 154(b) by 0 days.

(21) Appl. No.: 09/439,813

(22) Filed: Nov. 12, 1999

Related U.S. Application Data

(60) Provisional application No. 60/108,309, filed on Nov. 13, 1998, now abandoned.

(51) Int. Cl.$^7$ ............... A61K 39/04; A61K 39/395; A61K 39/40; A61K 39/02
(52) U.S. Cl. ............... 424/248.1; 424/141.1; 424/146.1; 424/150.1; 424/164.1; 424/168.1; 424/234.1; 435/252.1; 435/253.1; 435/863; 435/864; 435/865; 435/866; 514/924; 530/300; 530/350
(58) Field of Search ............... 424/141.1, 146.1, 424/150.1, 164.1, 168.1, 234.1, 248.1; 435/252.1, 253.1, 863, 864, 865, 866; 514/924; 530/300, 350

(56) References Cited

PUBLICATIONS

Beauchamp et al., "Superoxide Dismutase: Improved Assays and an Assay Applicable to Acrylamide Gels," Analytical Biochemistry, vol. 44, pp. 276–287, 1971.

GenBank Accession No. Z84724, Jun. 17, 1998.

Andersen et al., Proteins Released from Mycobacterium Tuberculosis During Growth, Infection and Immunity 1905–1910, 1991. vol. 59 No. 6.

Kusunose et al., "Superoxide Dismutase from Mycobacterium Tuberculosis", J. Biochem. 80:1343–1352, 1976.

Raynaud et al., "Extracellular Enzyme Activities Potentially Involved in the Pathogenicity of Mycobacterium Tuberculosis", Microbiology 144:577–587, 1998.

Rambukkana et al., "Identification of a Novel 27–kDa Protein from Mycobacterium Tuberculosis Culture Fluid by a Monoclonal Antibody Specific for the Mycobacterium Tuberculosis Complex", Scand. J. Immunol. 37:471–478, 1993.

Wu et al., "Identification and Subcellular Localization of a Novel Cu, Zn Superoxide Dismutase of Mycobacterium Tuberculosis", FEBS Letters 439:192–196, 1998.

*Primary Examiner*—Rodney P Swartz
(74) *Attorney, Agent, or Firm*—Fish & Richardson P.C.

(57) ABSTRACT

The invention relates to *Mycobacterium tuberculosis* superoxide dismutase antibodies, methods of using them for detection of *M. tuberculosis*, methods of testing for an inhibitor of an *M. tuberculosis* superoxide dismutase, and methods of detecting tuberculosis infection.

6 Claims, No Drawings

MYCOBACTERIUM TUBERCULOSIS SUPEROXIDE DISMUTASE

This application claims priority from U.S. Provisional Application Serial No. 60/108,309, filed Nov. 13, 1998, now abandoned.

BACKGROUND OF THE INVENTION

Superoxide dismutase catalyzes the conversion of superoxide radicals ($O_2^-$) into molecular oxygen ($O_2$) and hydrogen peroxide ($H_2O_2$). The conversion of superoxide radicals is generally beneficial to a cell, since such molecules can react with the cell's genomic DNA to induce mutations.

Superoxide dismutases (SOD) have been classified based on the inorganic atoms they require for activity. Three SOD families have been identified: those requiring manganese (MnSOD), those requiring iron (FeSOD), and those requiring copper and zinc (Cu, ZnSOD).

MnSODs have been found in mitochondria and prokaryotes, whereas FeSODs have been found in prokaryotes, primitive eukaryotes, and some plants. Cu, ZnSODs were originally found in eukaryotes and later found in several bacterial.

Macrophages are an important arm of a vertebrate's immune system. Such cells can kill pathogens such as bacteria by engulfing the pathogen and bombarding it with superoxide radicals. Therefore, a secreted Cu, ZnSOD may play a role in the survival of bacterial pathogens, especially those known to survive and grow in macrophages.

SUMMARY OF THE INVENTION

The invention is based on the discovery of a secreted Cu, ZnSOD in *Mycobacterium tuberculosis*. It has been found that antibodies which specifically bind this *M. tuberculosis* SOD are useful in detecting the presence of the bacterium. It has also been discovered that tuberculosis patients develop antibodies against the *M. tuberculosis* Cu,ZnSOD. Thus, a patient producing antibodies against *M. tuberculosis* Cu,ZnSOD is diagnostic for tuberculosis in that patient.

Accordingly, the invention features an antibody, such as a monoclonal antibody, which specifically binds to a polypeptide consisting of the amino acid sequence of SEQ ID NO:2, which is the amino acid sequence of the *M. tuberculosis* Cu,ZnSOD. Specific binding of an antibody to the polypeptide means that it does not substantially bind to other components within a sample. A Cu,ZnSOD or copper/zinc superoxide dismutase is a polypeptide that facilitates conversion of superoxide radicals to molecular oxygen and hydrogen peroxide, and whose superoxide dismutase activity is dependent on the presence of copper and zinc atoms or ions.

The invention also includes a method of detecting *M. tuberculosis* infection in a mammal by (1) providing a polypeptide comprising the amino acid sequence of SEQ ID NO:2; (2) contacting the polypeptide with a biological sample (e.g., a human serum sample) collected from the mammal, the contacting performed under conditions sufficient to allow an antibody to bind to the polypeptide; and (3) determining the presence of antibody bound to the polypeptide, wherein the presence of the antibody indicates *M. tuberculosis* infection in the mammal. This method optionally includes the step of removing antibodies which do not bind to the polypeptide.

The invention also features a method of testing whether a compound inhibits superoxide dismutase activity of a polypeptide by (1) contacting a polypeptide with the compound, the polypeptide being a Cu,ZnSOD (also called a copper/zinc superoxide dismutase) and having an amino acid sequence which is at least 50% (e.g., at least 60, 70, 80, 90 or 100%) identical to SEQ ID NO:2; (2) measuring the level of superoxide dismutase activity; and (3) comparing the level of superoxide dismutase activity in the presence of the compound with the level of superoxide dismutase activity in the absence of the compound. The compound is said to inhibit the superoxide dismutase activity of the polypeptide when the level of superoxide dismutase activity in the presence of the compound is lower than the level of superoxide dismutase activity in the absence of the compound. The polypeptide can be within a cell such as a bacterium, e.g., in the periplasm of the bacterium.

To facilitate the detection or testing methods of the invention, the polypeptide can be bound to a solid support (e.g., a plastic support such as a microtiter plate). In addition, the polypeptide can be covalently bound to a solid support bead such as Sepharose. The covalent linkage between the polypeptide and a support can be achieved by methods well known in the art. For example, the polypeptide can be covalently linked to a support by reacting it with chemically activated forms of the support (e.g., CNBr-activated Sepharose 4B or EAH Sepharose 4B, available from Pharmacia). In addition, equal amounts of the polypeptide can be deposited in each well of a microtiter plate, thereby creating an array on which multiple compounds can be tested in parallel or multiple samples can be assayed for the presence of *M. tuberculosis*.

DETAILED DESCRIPTION

The invention relates to an antibody useful for detecting *M. tuberculosis* in a sample, methods of detecting *M. tuberculosis* infection in a mammal, and methods of testing a compound for its ability to inhibit SOD activity. These aspects of the invention arise from the discovery of a novel Cu,ZnSOD produced by *M. tuberculosis*.

I. Polypeptides

The Cu,ZnSOD polypeptides useful in the methods of the invention include the *M. tuberculosis* Cu,ZnSOD polypeptide described below. The Cu,ZnSOD useful in the methods of the invention are not limited to the naturally occurring sequence. Cu,ZnSOD containing substitutions, deletions, or additions can also be used, provided that those polypeptides retain at least one activity associated with the naturally occurring polypeptide and are at least 50% identical to the naturally occurring sequence.

To determine the percent identity of two polypeptide sequences, the sequences are aligned for optimal comparison purposes (e.g., gaps can be introduced in the sequence of a first amino acid sequence for optimal alignment with a second amino acid sequence). The amino acid residues at corresponding amino acid positions are then compared. When a position in the first sequence is occupied by the same amino acid residue as the corresponding position in the second sequence, then the molecules are identical at that position. The percent identity between the two sequences is a function of the number of identical positions shared by the sequences (i.e., % identity=# of identical positions/total # of positions×100).

The determination of percent homology and identity between two sequences can be accomplished using a mathematical algorithm. An example of a mathematical algorithm utilized for the comparison of two sequences is the algorithm of Karlin et al., Proc Natl Acad Sci USA 87:2264–2268 (1990), modified as in Karlin et al., Proc Natl Acad Sci USA 90:5873–5877 (1993). Such an algorithm is incorporated into the NBLAST and XBLAST programs of Altschul et al., J Mol Biol 215:403–410 (1990). BLAST protein searches can be performed with the XBLAST program, score=50, wordlength=3 to obtain amino acid sequences homologous to protein molecules useful in the methods of the invention. To obtain gapped alignments for comparison purposes, Gapped BLAST can be utilized as described in Altschul et al., Nucleic Acids Res 25:3389–3402 (1997). When utilizing BLAST and Gapped BLAST programs, the default parameters of the respective programs (e.g., XBLAST and NBLAST) can be used. See http://www.ncbi.nlm.nih.gov. Another example of a mathematical algorithm utilized for the comparison of sequences is the algorithm of Myers et al., CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences is determined using any of the above-described techniques with allowances for gaps. In calculating percent identity, only exact matches are counted.

An example of a Cu,ZnSOD that is not naturally occurring, though useful in the methods of the invention, is a Cu,ZnSOD-glutathione-S-transferase fusion protein. Such a protein can be produced in large quantities in bacteria and easily isolated via glutathione affinity column. The fusion protein can then be used in an in vitro SOD assay in the presence or absence of a candidate inhibitor of SOD (i.e., a candidate M. tuberculosis antimicrobial agent).

II. Antibodies

The term "antibody" as used herein refers to immunoglobulin molecules and immunologically active portions of immunoglobulin molecules, i.e., molecules that contain an antigen binding site which specifically binds an antigen, such as M. tuberculosis Cu,ZnSOD. A molecule which specifically binds to M. tuberculosis Cu,ZnSOD is a molecule which binds M. tuberculosis Cu,ZnSOD, but does not substantially bind other molecules in a sample, e.g., a biological sample, which naturally contains M. tuberculosis Cu,ZnSOD. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind M. tuberculosis Cu,ZnSOD. The term "monoclonal antibody" or "monoclonal antibody composition", as used herein, refers to a population of antibody molecules that contain only one species of an antigen binding site capable of immunoreacting with a particular epitope of M. tuberculosis Cu,ZnSOD. A monoclonal antibody composition thus typically displays a single binding affinity for the M. tuberculosis Cu,ZnSOD protein with which it immunoreacts.

Polyclonal antibodies against M. tuberculosis Cu,ZnSOD can be prepared by immunizing a suitable subject with a M. tuberculosis Cu,ZnSOD immunogen. The anti-M. tuberculosis Cu,ZnSOD antibody titer in the immunized subject can be monitored over time by standard techniques, such as with an enzyme linked immunosorbent assay (ELISA) using immobilized M. tuberculosis Cu,ZnSOD. If desired, the antibody molecules directed against M. tuberculosis Cu,ZnSOD can be isolated from the mammal (e.g., from the blood) and further purified by well-known techniques, such as protein A chromatography to obtain the IgG fraction. At an appropriate time after immunization, e.g., when the anti-M. tuberculosis Cu,ZnSOD antibody titers are highest, antibody-producing cells can be obtained from the subject and used to prepare monoclonal antibodies by standard techniques, such as ones described in Kohler et al., Nature 256:495–497, 1975; Kozbor et al., Immunol Today 4:72, 1983; and Cole et al., Monoclonal Antibodies and Cancer Therapy, Alan R. Liss, Inc., pp. 77–96, 1985. The technology for producing various monoclonal antibody hybridomas is well known (see, e.g., Coligan et al., eds., Current Protocols in Immunology, John Wiley & Sons, Inc., New York, N.Y., 1994). Briefly, an immortal cell line (typically a myeloma) is fused to lymphocytes (typically splenocytes) from a mammal immunized with a M. tuberculosis Cu,ZnSOD immunogen as described above, and the culture supernatants of the resulting hybridoma cells are screened to identify a hybridoma producing a monoclonal antibody that binds M. tuberculosis Cu,ZnSOD.

Any of the many well known protocols used for fusing lymphocytes and immortalized cell lines can be applied for the purpose of generating an antibody against M. tuberculosis Cu,ZnSOD (see, e.g., Current Protocols in Immunology, supra; Galfre et al., Nature 266:55052, 1977; Kenneth, Monoclonal Antibodies: A New Dimension In Biological Analyses, Plenum Publishing Corp., New York, N.Y., 1980; and Lerner Yale J. Biol. Med., 54:387–402, 1981). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line, e.g., a myeloma cell line that is sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind M. tuberculosis Cu,ZnSOD, e.g., using a standard ELISA assay.

Alternative to preparing monoclonal antibody-secreting hybridomas, a monoclonal antibody against M. tuberculosis Cu,ZnSOD can be identified and isolated by screening a recombinant combinatorial immunoglobulin library (e.g., an antibody phage display library) with M. tuberculosis Cu,ZnSOD to thereby isolate immunoglobulin library members that bind M. tuberculosis Cu,ZnSOD. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication Nos. WO 92/18619, WO 91/17271, WO 92/20791, WO 92/15679, WO 93/01288, WO 92/01047, WO 92/09690, WO 90/02809; Fuchs et al., Bio/Technology 9:1370–1372, 1991; Hay et al., Hum Antibod Hybridomas 3:81–85, 1992; Huse et al., Science 246:1275–1281, 1989; and Griffiths et al., EMBO J 12:725–734, 1993.

Additionally, recombinant antibodies against *M. tuberculosis* Cu,ZnSOD, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT Publication Nos. WO 87/02671 and WO 86/01533; European Patent Application Nos. 184187, 171496, 173494, and 125023; U.S. Pat. Nos. 4,816,567 and 5,225,539; Better et al., Science 240:1041–1043, 1988; Liu et al., Proc Natl Acad Sci USA 84:3439–3443, 1987; Liu et al., J Immunol 139:3521–3526, 1987; Sun et al., Proc Natl Acad Sci USA 84:214–218, 1987; Nishimura et al., Canc Res 47:999–1005, 1987; Wood et al., Nature 314:446–449, 1985; Shaw et al., J Natl Cancer Inst 80:1553–1559, 1988; Morrison, Science 229:1202–1207, 1985; Oi et al., Bio/Techniques 4:214, 1986; Jones et al., Nature 321:552–525, 1986; Verhoeyan et al., Science 239:1534, 1988; and Beidler et al., J Immunol 141:4053–4060, 1988.

An antibody against *M. tuberculosis* Cu,ZnSOD (e.g., monoclonal antibody) can be used to isolate *M. tuberculosis* Cu,ZnSOD by standard techniques, such as affinity chromatography or immunoprecipitation. An antibody against *M. tuberculosis* Cu,ZnSOD can facilitate the purification of natural *M. tuberculosis* Cu,ZnSOD from the bacteria and of recombinantly produced *M. tuberculosis* Cu,ZnSOD expressed in host cells. Moreover, an anti-*M. tuberculosis* Cu,ZnSOD antibody can be used to detect *M. tuberculosis* Cu,ZnSOD protein (e.g., in a cellular lysate or serum sample) in order to evaluate the abundance of the *M. tuberculosis* Cu,ZnSOD protein. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase. Examples of suitable prosthetic group complexes include streptavidin/biotin and avidin/biotin. Examples of suitable fluorescent materials include umbelliferone, fluorescein, fluorescein isothiocyanate, rhodamine, dichlorotriazinylamine fluorescein, dansyl chloride or phycoerythrin. An example of a luminescent material includes luminol. Examples of bioluminescent materials include luciferase, luciferin, and aequorin. Examples of suitable radioactive material include $^{125}$I, $^{131}$I, $^{35}$S or $^{3}$H.

III. Contacting a Compound with a Cu,ZnSOD

For in vitro assays, contacting the compound with the Cu,ZnSOD can occur by mixing the Cu,ZnSOD with the compound in a solution, suspension, or gel. This solution, suspension, or gel is then subjected to a SOD assay.

For cellular assays, any Cu,ZnSOD polypeptide can be expressed in a cell if the cell does not already express Cu,ZnSOD, or overexpressed in the cell if the cell already expresses Cu,ZnSOD. Methods of expressing proteins in a cell are well known in the art.

If the Cu,ZnSOD resides within a cell, the compound can be delivered into the cell by methods well known in the art. If the compound is a membrane-permeable molecule, then the compound can be directly mixed with the cell, allowing contact between the Cu,ZnSOD and the compound. If the compound is not membrane permeable, as is expected for many macromolecules, the compound can be delivered into the cell by electroporation, or if it is a polypeptide, a nucleic acid or viral vector.

In addition, the cell can be an animal cell in vivo. Delivery of a compound to the cell can be accomplished by any route known in the art, including intravenous injection. Alternatively, a polypeptide compound can be administered by a nucleic acid or viral vector if delivery into the cell is desired.

IV. Superoxide Dismutase Assays

Assays for superoxide dismutase activity can be determined by any standard technique know in the art. See, for example the assays described in Beauchamp et al., Anal Biochem 44:276–287, 1971; and references therein.

Many of these assays rely on photoreduction of nitro blue tetrazolium (NBT), a process mediated by the production of superoxide radicals. Superoxide dismutase activity is reflected in any inhibition of the reduction of NBT. Exposure to an appropriate light source will turn NBT into a blue dye readily quantifiable by its absorbance at 560 nm. In the presence of a superoxide dismutase, however, photoreduction of NBT to a blue dye will be decreased or eliminated. Specific procedures based on this general concept are well known in the art. See, for example, the procedure described below.

Without further elaboration, it is believed that one skilled in the art can, based on the above disclosure and the description below, utilize the present invention to its fullest extent. The following examples are to be construed as merely illustrative of how one skilled in the art can practice the invention and are not limitative of the remainder of the disclosure in any way. Any publications cited in this disclosure are hereby incorporated by reference.

EXAMPLE 1

Cloning and Characterization of the *Mycobacterium tuberculosis* Cu,ZnSOD

*E. coli* strains XL1 blue (Stratagen) and BL21(DE3) (Novagen) were used for cloning and over-expression of recombinant proteins, respectively. *M. tuberculosis* H37Rv was used for the electron microscopic analysis.

Cloning procedures were carried out according to standard protocols. Fragments of the sodC gene were PCR amplified from genomic DNA of *M. tuberculosis* using oligonucleotide pairs 5'-CATATGTCTACAGTTCCGGGTACCA-3' (SEQ ID NO:3) and 5'-GGATCCAAGCTAGCCGGAACCAATGA-3' (SEQ ID NO:4) for the full-length clone, and 5'-CATATGCCAAAGCCCGCCGATCA-3' (SEQ ID NO:5) and 5'-GGATCCAAGCTAGCCGGAACCAATGA-3' (SEQ ID NO:6), for a truncated form (described below). The PCR products were cloned into the T-vector pT7-Blue (Novagene) and subsequently subcloned into the NdeI and BamHI sites of the expression vector pET15B (Novagene). Both strands of the cloned fragments were sequenced using the ABI BigDye (PE Applied Biosystems) fluorescence sequencing chemistry according to manufacturer's instructions, and an ABI PRISM 310 Genetic Analyzer automatic sequencer (PE Applied Biosystems).

Sequencing revealed that the sodC gene contained the following open reading frame:

ATGCCAAAGCCCGCCGATCACCGCAAT-
CACGCAGCTGTCAGCACG TCGGTCCTGTC-
CGCGTTGTTTCTGGGCGCCGGTGC-
CGCGCTGCTG

AGCGCATGCTCGTCGCCGCAG-
CACGCGTCTACAGTTCCGGGTACC ACGC-
CGTCGATTTGGACCGGATCGCCCGCGC-
CGTCGGGACTTTCG
GGTCACGACGAGGAGTCGCCCGGTGCG-
CAGAGCCTGACCAGTACC CTGACGGCGC-
CCGACGGCACGAAGGTAGCGACCGC-
GAAGTTCGAG
TTCGCCAACGGCTATGCCACCGTCAC-
GATCGCGACGACCGGCGTC GGTAAGCT-
CACGCCCGGCTTCCACGGCCTACACATC-
CACCAGGTG
GGTAAGTGTGAGCCCAACTCGGTTGC-
CCCCACCGGCGGTGCGCCC GGCAACTTTCT-
GTCCGCCGGCGGCCACTACCACGTGC-
CAGGGCAT
ACCGGCACCCCCGCCAGCGGCGACCTG-
GCCTCGCTGCAGGTACGC GGTGACGGTTCG-
GCGATGCTGGTGACCACCACCGACGCCT-
TCACC
ATGGACGACCTGCTGAGCGGCGC-
GAAAACCGCGATCATCATTCAC GCCGGCGC-
CGACAACTTTGCCAACATTCCGCCA-
GAACGCTACGTC
CAGGTCAATGGGACTCCGGGTCCCGAC-
GAGACGACGTTGACCACC GGCGACGCCG-
GCAAGCGGGTGGCGTGCGGTGTCATTG-
GTTCCGGC (SEQ ID NO:1).

The open reading frame is terminated by a natural TAG stop codon immediately following the above sequence. This open reading frame encoded a 240 amino acid polypeptide having the following sequence:

MPKPADHRNHAAVSTSVLSALFLGAGAALLSACSSP
QHASTVPGTTPSIWTGSPAPSGLSGHDEESPGA
QSLTSTLTAPDGTKVATAKFEFANGYATVTIAT
TGVGKLTPGFHGLHIHQVGKCEPNSVAPTGGAP
GNFLSAGGHYHVPGHTGTPASGDLASLQVR
GDGSAMLVTTTDAFTMDDLLSGAKTAIIIHAGA
DNFANIPPERYVQVNGTPGPDETTLTT GDAGKR
VACGVIGSG (SEQ ID NO:2).

Using the PSORT program analysis (http://psort.nibb.ac.jp/), a putative signal peptide (underlined above) was found at the N-terminus of this polypeptide.

pET15b expression vectors encoding versions of the above SOD were used to transform BL21 (DE3) cells. The L-sodC plasmid includes SEQ ID NO:1. The S-sodC plasmid includes nucleotides 118–720 of SEQ ID NO:1, excluding the sequence encoding the signal peptide. The M-sodC includes nucleotides 118–720, with a T to A mutation in the natural stop codon so that a Lys is encoded. An additional sequence downstream of the codon encoding the new Lys was then added (CCGAATTCCAGCACACTG GCGGC-CGTTACTAGTGGATCCGGCTGCTAA; SEQ ID NO:7), thereby encoding the additional amino acid sequence PNS-STLAAVTSGSGC (SEQ ID NO:8). Expression of the recombinant proteins were induced by incubating the BL21 (DE3) bacterium carrying the recombinant sodC plasmid in LB broth containing 0.5 mM IPTG at 37° C. for 100 minutes. The bacteria were harvested by centrifugation and lysed via sonication in 10 mM phosphate buffer (pH 7.4) and 10 mM imidazole. The recombinant proteins in the inclusion bodies were denatured and solubilized in 20 mM Tris-HCl (pH 8.0), 100 mM NaCl, 8 M urea, and 50 mM imidazole. The proteins were then purified on a His-Trap-Chelating column (Pharmacia) according to manufacturer's instructions. The purified recombinant proteins were renatured by dialysis against 50 mM Tris-HCl pH 7.8, 1 mM $CuSO_4$, and 1 mM $ZnSO_4$ at 4° C., with several changes of dialysate. The purified proteins were stored in dialysate supplemented with 20% glycerol. The recombinant proteins which were soluble in the cell-free extracts were purified using the same column under native conditions (i.e., with dialysate free of $CuSO_4$).

The majority of the overexpressed proteins were present in the insoluble inclusion body upon IPTG induction. These proteins in the inclusion bodies were denatured, solubilized with urea, and purified to near homogeneity, as indicated on a SDS-PAGE gel stained with Coomassie brilliant blue R-250. A minor fraction of these proteins were also purified in a soluble form from the cell lysates. The SDS-PAGE also revealed that L-sodC exhibited a MW of about 28–32 kDa, M-sodC exhibited a MW of about 26 kDa, and S-sodC exhibited a MW of about 24–25 kDa.

M-sodC was prepared for antibody production by fractionating the affinity-purified M-sodC on a SDS-PAGE gel stained with Coomassie brilliant blue R-250. A gel slice containing the M-sodC protein was mixed with complete Freund's adjuvant, and the mixture used to immunized 3-month old New Zealand white rabbits. The initial immunization was followed by three boosters with protein mixed with incomplete Freund's adjuvant. Antisera were collected at a 10-day intervals starting from the last boost.

Protein samples to be analyzed were fractionated on a SDS-PAGE gel, electrotransferred to an Immobilon TM-P membrane (Millipore), and subjected to detection with rabbit antiserum followed by horseradish peroxidase-conjugated donkey anti-rabbit IgG antibody (Amersham). Target bands were detected with the enhanced chemiluminescence kit (ECL, Amersham) and recorded on Hyperfilm-MP film (Amersham).

Rabbit polyclonal antisera against the purified recombinant M-sodC protein recognized all three forms of the SOD proteins and did not cross-react with the sodC gene product of *E. coli*. More significantly, the antisera recognized a single polypeptide of about 26 kDa in size in *M. tuberculosis* lysates, substantiating that the sodC sequence expresses protein. This finding also suggests that the *M. tuberculosis* SOD was processed into a mature form, as predicted above, and secreted.

To assess SOD enzymatic activity of the recombinant proteins, bacteria expressing the proteins were resuspended in 50 mM phosphate buffer (pH 7.8) and 0.1 mM EDTA, sonicated, and centrifuged to obtain bacterial extracts. SOD activity was assayed by separating the extracts on a 10% non-denaturing polyacrylamide gel, staining with NBT, and exposing to light as described in Beauchamp, supra. 1 mM KCN was known to selectively inhibit Cu,ZnSOD activity, and so was added to control samples to confirm that the SOD activity was due to a Cu,ZnSOD enzyme.

The majority of the *M. tuberculosis* Cu,ZnSOD expressed in *E. coli* were found in the insoluble inclusion bodies and did not possess any enzymatic activity. To reconstitute the enzymatic activity, purified recombinant proteins prepared from the inclusion bodies were denatured with urea and renatured by dialysis in a solution of $Cu^{2+}$ and $Zn^{2+}$. The renatured recombinant M-sodC protein purified from the inclusion bodies formed multiple white bands on the blue NBT-stained gel. These bands may represent multiple conformations of the active recombinant protein.

Recombinant Cu,ZnSOD (S-sodC) purified from the soluble cytoplasmic fraction was represented by a single white band on the blue NBT-stained gel. White bands representing *M. tuberculosis* Cu,ZnSOD (S-sodC), yeast Cu,ZnSOD, and renatured forms of *M. tuberculosis* Cu,ZnSOD (M-sodC) were all abolished when the gel was stained in the presence of 1 mM KCN. This result demonstrated that the protein encoded by the *M. tuberculosis* sodC gene encoded a bona fide Cu,Zn-cofactored superoxide dismutase.

To determine the cellular compartmentalization of the Cu,ZnSOD, the L-sodC enzyme was expressed in *E. coli*, and the bacteria subjected to immunogold labeling electron microscopy as follows. Preparation of 15 nm colloidal gold-IgG complex and immunogold labeling were performed as described in Lin et al., J Ultrastruct Res 84:16–23, 1983; and Chang et al., J Gen Virol 78:1175–1179, 1997. Briefly, several M. tuberculosis colonies were scraped from an agar slant and fixed in 1% formaldehyde and 0.1 M phosphate-citrate buffer (pH 7.2) at 4° C. overnight. The fixed samples were neutralized with 0.1 M ammonium chloride and 0.1 M phosphate-citrate buffer (pH 7.2) at 0° C. for 30 min. This neutralization was followed by dehydration through a series of methanol washes, first with 50% methanol at 0° C. for 15 minutes, then repeated with 75% and 90% methanol, and then two 100% methanol washes at −20° C. for 1 hour for each wash. The dehydrated samples were infiltrated with a graded series of embedding agent LR Gold. The samples were first infiltrated by immersion in 25% LR Gold, 10% PVP-6,000 at −20° C. for 1 hour. Then the sample was immersed in 50% LR Gold, 10% PVP-6,000 at −20° C. for 2 hours, followed by 75% LR Gold at −20° C. for 4 hours. Finally, the samples were fully infiltrated with 100% LR Gold at −20° C. overnight. Polymerization of the embedding agent was initiated with long wave UV irradiation at −20° C. for 24 hours, and the samples hardened at room temperature for 24 hours. Ultrathin sections (100 nm) of the LR Gold-embedded samples were mounted on 200 mesh nickel grids covered with carbon-backed collodion film. Sections on the grids were blocked with 3% normal goat serum in PBS for 10 minutes, incubated with the rabbit antiserum against Cu,Zn—SOD (see above) for 15 minutes, washed with 1% normal goat serum in PBS, and incubated with the colloidal gold-IgG complex for 10 min. The grids were washed extensively with triple glass-distilled water before contrasting with uranyl acetate and lead citrate. The sections were examined with a Zeiss EM109 electron microscope (Zeiss, Germany).

Since the periplasmic space is not present in the Gram-positive *M. tuberculosis*, secretion of the Cu,ZnSOD to the periphery of the bacterium was examined. Using immunogold labeling and electron microscopy, the Cu,ZnSOD was shown to be predominantly localized to the periphery of *M. tuberculosis*. This result is consistent with the findings described above, namely that (1) the Cu,ZnSOD possessed a putative signal peptide sequence, and (2) the mature, naturally occurring Cu,ZnSOD exhibited a size similar to that of the truncated S-sodC protein on SDS-PAGE gels. These data suggest that *M. tuberculosis* Cu,ZnSOD is either secreted or attached to the outer surface of the bacterium.

In a separate experiment, *M. tuberculosis* Cu,ZnSOD was expressed in *E. coli*. Localization of the expressed protein was then determined using immunogold labelling electron microscopy as described above. Staining indicated that the Cu,ZnSOD was predominantly localized to the periplasmic space of the bacteria. Thus, this protein can be recombinantly produced and secreted in cells suitable for large scale production of the protein.

EXAMPLE 2

Enzyme-Linked Immunosorbant Assay for Detecting *Mycobacterium tuberculosis*

Since the *M. tuberculosis* Cu,ZnSOD is exposed to the exterior of the cell, an ELISA detection assay was developed using antibodies specific for the Cu,ZnSOD. The wells were coated with 1.22, 4.88, 19.5, 78.1, 312, or 1250 ng/ml solutions of S-sodC by incubating at 4° C. overnight. The protein was then removed, and the wells blocked with 10% fetal calf serum in PBST at 37° C. for two hours. The wells were washed 3× with PBST, and a 1:400 dilution of the rabbit antiserum obtained in Example 1 above was added. The rabbit antibodies were incubated in the wells at 4° C. overnight. Afterwards, the wells were washed 3× with PBST, and a 1:1000 dilution of horseradish peroxidase-conjugated donkey anti-rabbit antibody (Amersham, Cat. No. NA943) was added. The donkey antibody was incubated in the wells at 37° C. for six hours. The wells were again washed 3× with PBST, and the color developed by adding TMB (KPL, Inc.) and incubating at room temperature for less than 30 minutes, the reactions were stopped by adding 1 M $H_3PO_4$.

Absorbance readings at 450 nm indicated a dynamic or quantifiable detection range between about 10 ng and 1000 ng. For samples containing more than 1000 ng, the readings were no longer dynamic. This result indicated that a useful ELISA detection method for *M. tuberculosis* can be developed using antibodies specific for the Cu,ZnSOD described above.

EXAMPLE 3

Detection of *Mycobacterium tuberculosis* Infection

Given that the *M. tuberculosis* Cu,ZnSOD was exposed to the extracellular environment, the ability of tuberculosis (TB) patients to generate antibodies against Cu,ZnSOD was examined. TB patient sera were used to detect the *M. tuberculosis* Cu,ZnSOD described above in Western blots. The results indicated that 12 out of 110 patients produced antibodies against the *M. tuberculosis* Cu,ZnSOD, indicating that the presence of antibodies against this protein in an individual can be used as a surrogate marker for TB.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of this invention.

What is claimed is:

1. A method of detecting *Mycobacterium tuberculosis* infection in a mammal, the method comprising:
   providing a polypeptide consisting essentially of the amino acid sequence of SEQ ID NO:2;
   contacting the polypeptide with a biological sample collected from the mammal, the contacting performed under conditions sufficient to allow an antibody to bind to the polypeptide; and
   detecting the antibody bound to the SEQ ID NO:2 region of the polypeptide, wherein the presence of the antibody indicates *Mycobacterium tuberculosis* infection in the mammal.

2. The method of claim 1, further comprising removing antibodies which do not bind to the polypeptide.

3. The method of claim 1, wherein the polypeptide is bound to a solid support.

4. The method of claim 3, wherein the solid support is plastic.

5. The method of claim 3, wherein the polypeptide is covalently bound to the solid support.

6. The method of claim 1, wherein the mammal is a human, and the biological sample is a human serum sample.

* * * * *

SEQUENCE LISTING

```
<160> NUMBER OF SEQ ID NOS: 8

<210> SEQ ID NO 1
<211> LENGTH: 720
<212> TYPE: DNA
<213> ORGANISM: Mycobacterium tuberculosis
<220> FEATURE:
<221> NAME/KEY: CDS
```

<222> LOCATION: (1)...(720)

<400> SEQUENCE: 1

| | | | | | | | | | | | | | | | | |
|---|---|---|---|---|---|---|---|---|---|---|---|---|---|---|---|---|
| atg | cca | aag | ccc | gcc | gat | cac | cgc | aat | cac | gca | gct | gtc | agc | acg | tcg | 48 |
| Met | Pro | Lys | Pro | Ala | Asp | His | Arg | Asn | His | Ala | Ala | Val | Ser | Thr | Ser | |
| 1 | | | | 5 | | | | | 10 | | | | | 15 | | |
| gtc | ctg | tcc | gcg | ttg | ttt | ctg | ggc | gcc | ggt | gcc | gcg | ctg | ctg | agc | gca | 96 |
| Val | Leu | Ser | Ala | Leu | Phe | Leu | Gly | Ala | Gly | Ala | Ala | Leu | Leu | Ser | Ala | |
| | | | 20 | | | | | 25 | | | | | 30 | | | |
| tgc | tcg | tcg | ccg | cag | cac | gcg | tct | aca | gtt | ccg | ggt | acc | acg | ccg | tcg | 144 |
| Cys | Ser | Ser | Pro | Gln | His | Ala | Ser | Thr | Val | Pro | Gly | Thr | Thr | Pro | Ser | |
| | | 35 | | | | | 40 | | | | | 45 | | | | |
| att | tgg | acc | gga | tcg | ccc | gcg | ccg | tcg | gga | ctt | tcg | ggt | cac | gac | gag | 192 |
| Ile | Trp | Thr | Gly | Ser | Pro | Ala | Pro | Ser | Gly | Leu | Ser | Gly | His | Asp | Glu | |
| | 50 | | | | | 55 | | | | | 60 | | | | | |
| gag | tcg | ccc | ggt | gcg | cag | agc | ctg | acc | agt | acc | ctg | acg | gcg | ccc | gac | 240 |
| Glu | Ser | Pro | Gly | Ala | Gln | Ser | Leu | Thr | Ser | Thr | Leu | Thr | Ala | Pro | Asp | |
| 65 | | | | | 70 | | | | | 75 | | | | | 80 | |
| ggc | acg | aag | gta | gcg | acc | gcg | aag | ttc | gag | ttc | gcc | aac | ggc | tat | gcc | 288 |
| Gly | Thr | Lys | Val | Ala | Thr | Ala | Lys | Phe | Glu | Phe | Ala | Asn | Gly | Tyr | Ala | |
| | | | | 85 | | | | | 90 | | | | | 95 | | |
| acc | gtc | acg | atc | gcg | acg | acc | ggc | gtc | ggt | aag | ctc | acg | ccc | ggc | ttc | 336 |
| Thr | Val | Thr | Ile | Ala | Thr | Thr | Gly | Val | Gly | Lys | Leu | Thr | Pro | Gly | Phe | |
| | | | 100 | | | | | 105 | | | | | 110 | | | |
| cac | ggc | cta | cac | atc | cac | cag | gtg | ggt | aag | tgt | gag | ccc | aac | tcg | gtt | 384 |
| His | Gly | Leu | His | Ile | His | Gln | Val | Gly | Lys | Cys | Glu | Pro | Asn | Ser | Val | |
| | | 115 | | | | | 120 | | | | | 125 | | | | |
| gcc | ccc | acc | ggc | ggt | gcg | ccc | ggc | aac | ttt | ctg | tcc | gcc | ggc | ggc | cac | 432 |
| Ala | Pro | Thr | Gly | Gly | Ala | Pro | Gly | Asn | Phe | Leu | Ser | Ala | Gly | Gly | His | |
| | 130 | | | | | 135 | | | | | 140 | | | | | |
| tac | cac | gtg | cca | ggg | cat | acc | ggc | acc | ccc | gcc | agc | ggc | gac | ctg | gcc | 480 |
| Tyr | His | Val | Pro | Gly | His | Thr | Gly | Thr | Pro | Ala | Ser | Gly | Asp | Leu | Ala | |
| 145 | | | | | 150 | | | | | 155 | | | | | 160 | |
| tcg | ctg | cag | gta | cgc | ggt | gac | ggt | tcg | gcg | atg | ctg | gtg | acc | acc | acc | 528 |
| Ser | Leu | Gln | Val | Arg | Gly | Asp | Gly | Ser | Ala | Met | Leu | Val | Thr | Thr | Thr | |
| | | | | 165 | | | | | 170 | | | | | 175 | | |
| gac | gcc | ttc | acc | atg | gac | gac | ctg | ctg | agc | ggc | gcg | aaa | acc | gcg | atc | 576 |
| Asp | Ala | Phe | Thr | Met | Asp | Asp | Leu | Leu | Ser | Gly | Ala | Lys | Thr | Ala | Ile | |
| | | | 180 | | | | | 185 | | | | | 190 | | | |
| atc | att | cac | gcc | ggc | gcc | gac | aac | ttt | gcc | aac | att | ccg | cca | gaa | cgc | 624 |
| Ile | Ile | His | Ala | Gly | Ala | Asp | Asn | Phe | Ala | Asn | Ile | Pro | Pro | Glu | Arg | |
| | | 195 | | | | | 200 | | | | | 205 | | | | |
| tac | gtc | cag | gtc | aat | ggg | act | ccg | ggt | ccc | gac | gag | acg | acg | ttg | acc | 672 |
| Tyr | Val | Gln | Val | Asn | Gly | Thr | Pro | Gly | Pro | Asp | Glu | Thr | Thr | Leu | Thr | |
| | 210 | | | | | 215 | | | | | 220 | | | | | |
| acc | ggc | gac | gcc | ggc | aag | cgg | gtg | gcg | tgc | ggt | gtc | att | ggt | tcc | ggc | 720 |
| Thr | Gly | Asp | Ala | Gly | Lys | Arg | Val | Ala | Cys | Gly | Val | Ile | Gly | Ser | Gly | |
| 225 | | | | | 230 | | | | | 235 | | | | | 240 | |

<210> SEQ ID NO 2
<211> LENGTH: 240
<212> TYPE: PRT
<213> ORGANISM: Mycobacterium tuberculosis

<400> SEQUENCE: 2

| | | | | | | | | | | | | | | | |
|---|---|---|---|---|---|---|---|---|---|---|---|---|---|---|---|
| Met | Pro | Lys | Pro | Ala | Asp | His | Arg | Asn | His | Ala | Ala | Val | Ser | Thr | Ser |
| 1 | | | | 5 | | | | | 10 | | | | | 15 | |

| | | | | | | | | | | | | | | | |
|---|---|---|---|---|---|---|---|---|---|---|---|---|---|---|---|
| Val | Leu | Ser | Ala | Leu | Phe | Leu | Gly | Ala | Gly | Ala | Ala | Leu | Leu | Ser | Ala |
| | | | 20 | | | | | 25 | | | | | 30 | | |

| | | | | | | | | | | | |
|---|---|---|---|---|---|---|---|---|---|---|---|
| Cys | Ser | Ser | Pro | Gln | His | Ala | Ser | Thr | Val | Pro | Gly | Thr | Thr | Pro | Ser |

```
                 35                  40                  45
Ile Trp Thr Gly Ser Pro Ala Pro Ser Gly Leu Ser Gly His Asp Glu
 50                  55                  60

Glu Ser Pro Gly Ala Gln Ser Leu Thr Ser Thr Leu Thr Ala Pro Asp
 65                  70                  75                  80

Gly Thr Lys Val Ala Thr Ala Lys Phe Glu Phe Ala Asn Gly Tyr Ala
                     85                  90                  95

Thr Val Thr Ile Ala Thr Thr Val Gly Lys Leu Thr Pro Gly Phe
                100                 105                 110

His Gly Leu His Ile His Gln Val Gly Lys Cys Glu Pro Asn Ser Val
                115                 120                 125

Ala Pro Thr Gly Ala Pro Gly Asn Phe Leu Ser Ala Gly Gly His
130                 135                 140

Tyr His Val Pro Gly His Thr Gly Thr Pro Ala Ser Gly Asp Leu Ala
145                 150                 155                 160

Ser Leu Gln Val Arg Gly Asp Gly Ser Ala Met Leu Val Thr Thr Thr
                165                 170                 175

Asp Ala Phe Thr Met Asp Asp Leu Leu Ser Gly Ala Lys Thr Ala Ile
                180                 185                 190

Ile Ile His Ala Gly Ala Asp Asn Phe Ala Asn Ile Pro Pro Glu Arg
                195                 200                 205

Tyr Val Gln Val Asn Gly Thr Pro Gly Pro Asp Glu Thr Thr Leu Thr
210                 215                 220

Thr Gly Asp Ala Gly Lys Arg Val Ala Cys Gly Val Ile Gly Ser Gly
225                 230                 235                 240

<210> SEQ ID NO 3
<211> LENGTH: 25
<212> TYPE: DNA
<213> ORGANISM: Artificial Sequence
<220> FEATURE:
<223> OTHER INFORMATION: primer for PCR

<400> SEQUENCE: 3
catatgtcta cagttccggg tacca                                    25

<210> SEQ ID NO 4
<211> LENGTH: 26
<212> TYPE: DNA
<213> ORGANISM: Artificial Sequence
<220> FEATURE:
<223> OTHER INFORMATION: primer for PCR

<400> SEQUENCE: 4
ggatccaagc tagccggaac caatga                                   26

<210> SEQ ID NO 5
<211> LENGTH: 23
<212> TYPE: DNA
<213> ORGANISM: Artificial Sequence
<220> FEATURE:
<223> OTHER INFORMATION: primer for PCR

<400> SEQUENCE: 5
catatgccaa agcccgccga tca                                      23

<210> SEQ ID NO 6
<211> LENGTH: 26
<212> TYPE: DNA
<213> ORGANISM: Artificial Sequence
```

```
<220> FEATURE:
<223> OTHER INFORMATION: primer for PCR

<400> SEQUENCE: 6
ggatccaagc tagccggaac caatga                                              26

<210> SEQ ID NO 7
<211> LENGTH: 48
<212> TYPE: DNA
<213> ORGANISM: Mycobacterium tuberculosis
<220> FEATURE:
<221> NAME/KEY: CDS
<222> LOCATION: (1)...(45)

<400> SEQUENCE: 7 ccg aat tcc agc aca ctg gcg gcc gtt act agt gga tcc ggc tgc               45
Pro Asn Ser Ser Thr Leu Ala Ala Val Thr Ser Gly Ser Gly Cys
 1               5                  10                  15 taa                                                                        48

<210> SEQ ID NO 8
<211> LENGTH: 15
<212> TYPE: PRT
<213> ORGANISM: Mycobacterium tuberculosis

<400> SEQUENCE: 8

Pro Asn Ser Ser Thr Leu Ala Ala Val Thr Ser Gly Ser Gly Cys
 1               5                  10                  15
```